United States Patent
Kakuma (10) Patent No.: US 10,555,673 B2
(45) Date of Patent: Feb. 11, 2020

(54) PROBE, OPTICAL COHERENCE TOMOGRAPHY DEVICE, AND ZERO POINT CORRECTION METHOD

(71) Applicant: THE YOSHIDA DENTAL MFG. CO., LTD., Tokyo (JP)

(72) Inventor: Hideo Kakuma, Tokyo (JP)

(73) Assignee: THE YOSHIDA DENTAL MFG. CO., LTD., Tokyo (JP)

( * ) Notice: Subject to any disclaimer, the term of this patent is extended or adjusted under 35 U.S.C. 154(b) by 498 days.

(21) Appl. No.: 15/326,334

(22) PCT Filed: Jul. 6, 2015

(86) PCT No.: PCT/JP2015/069442
§ 371 (c)(1),
(2) Date: Jan. 13, 2017

(87) PCT Pub. No.: WO2016/009878
PCT Pub. Date: Jan. 21, 2016

(65) Prior Publication Data
US 2017/0196460 A1 Jul. 13, 2017

(30) Foreign Application Priority Data
Jul. 17, 2014 (JP) ................. 2014-147150

(51) Int. Cl.
*A61B 5/00* (2006.01)
*A61B 1/24* (2006.01)

(52) U.S. Cl.
CPC .............. *A61B 5/0066* (2013.01); *A61B 1/24* (2013.01); *A61B 5/742* (2013.01)

(58) Field of Classification Search
CPC .. A61B 5/0066; A61B 5/0088; G01B 9/02091
See application file for complete search history.

(56) References Cited

U.S. PATENT DOCUMENTS

| | | | |
|---|---|---|---|
| 2004/0147843 A1* | 7/2004 | Bambot ............... | A61B 5/0071 600/473 |
| 2006/0149154 A1* | 7/2006 | Stephens .............. | A61B 5/0059 600/504 |

(Continued)

FOREIGN PATENT DOCUMENTS

| | | |
|---|---|---|
| EP | 2692274 A1 | 2/2014 |
| JP | 2012-213433 A | 11/2012 |

(Continued)

OTHER PUBLICATIONS

Search Report for European Patent Application No. 15822467.5, dated Mar. 7, 2018.

(Continued)

*Primary Examiner* — Eric D. Bertram
(74) *Attorney, Agent, or Firm* — Merchant & Gould P.C.

(57) ABSTRACT

A probe (1) is used in an optical coherence tomography device which irradiates measurement light to a subject and collects scattered light that has returned from the subject after being reflected. The probe (1) is provided with a scanning means (70) composed of galvanometer mirrors (72, 73) that change an irradiation direction of the measurement light. The scanning means (70) is provided with actuators (72b, 73b) which switch reflecting mirrors (72a, 73a) that reflect the measurement light between a state where the measurement light is reflected by the subject and returns as the scattered light, and a state where the measurement light is diffusely reflected within the probe (1).

8 Claims, 8 Drawing Sheets (56) References Cited

U.S. PATENT DOCUMENTS

2009/0079993 A1* 3/2009 Yatagai ............... A61B 5/0062
356/497
2013/0242258 A1 9/2013 Higuchi
2014/0192323 A1* 7/2014 Kakuma ............... A61B 3/102
351/206

FOREIGN PATENT DOCUMENTS

| JP | 2012-217752 A | 11/2012 |
| JP | 2012-217753 A | 11/2012 |
| WO | 2010/098204 A1 | 9/2010 |

OTHER PUBLICATIONS

International Search Report for PCT/2015/069442, dated Sep. 29, 2015.

* cited by examiner

PROBE, OPTICAL COHERENCE TOMOGRAPHY DEVICE, AND ZERO POINT CORRECTION METHOD

CROSS-REFERENCE TO RELATED APPLICATION

This application is a U.S. National Stage Application under 35 U.S.C. § 371 of International Patent Application No. PCT/JP2015/069442 filed Jul. 6, 2015, which claims the benefit of priority to Japanese Patent Application No. 2014-147150 filed Jul. 17, 2014, the disclosures of all of which are hereby incorporated by reference in their entireties. The International Application was published in Japanese on Jan. 21, 2016 as WO 2016/009878.

TECHNICAL FIELD

The present invention relates to a probe, an optical coherence tomography device, and a zero point correction method, the probe being used in the optical coherence tomography device which captures a tomographic image inside an object by utilizing optical coherence.

BACKGROUND ART

Conventionally, an optical coherence tomography device for dentistry (hereinafter, referred to as an OCT device) divides a laser light emitted from a light source into reference light and measurement light, and irradiates the measurement light to oral tissue from a probe (hand piece) while irradiating the reference light to a reference mirror. Further, the OCT device collects scattered light returning after reflection from the oral tissue by the probe, combines the scattered light and a reflected light from the reference mirror by an optical multiplexer, and analyzes interference light thereof, to generate a tomographic image (for example, see Patent Document 1).

The probe (diagnostic probe portion) of the OCT device described in Patent Document 1 is internally provided with a shutter mechanism for blocking the measurement light by a shutter when performing zero point correction for removing by software noise (image) of image data displayed on a display screen. The zero point correction is to obtain background data in a state of blocking an optical path of the measurement light by closing the shutter, and to obtain a zero point by subtracting the noise generated in the background from measurement data measured by the probe, so that the image is adjusted to appear clearly.

The shutter mechanism is a device for blocking the measurement light sent from a circulator and the scattered light, which is the measurement light reflected from a subject, from passing through the probe. The shutter mechanism is interposed between a collimator lens in a grip portion of the probe and a scanning means in a scanning means housing portion.

Besides the shutter mechanism, as a method of blocking all reflected signals from the subject and creating a state for receiving only a signal from a reference, it is considered to create a state in which a light reflected from the subject does not return by irradiating the measurement light while directing the probe toward the air so that the measurement light does not hit the subject or other objects.

CITATION LIST

Patent Literature

{Patent Document 1}
Japanese Patent Application Publication No. 2012-217753

SUMMARY OF INVENTION

Technical Problem

Since the probe described in Patent Document 1 is provided with the shutter mechanism in a housing of the probe, there has been a problem that the number of components and the number of assembly steps are increased by providing the shutter mechanism, and thus a structure of the probe is complicated and the cost is increased.

Further, the conventional probe including a means for blocking all the reflected signals from the subject other than the shutter mechanism described above has a possibility of irradiating a laser to a patient by mistake when irradiating the laser toward the air.

Therefore, the present invention has been made in order to solve such problems, and an object of the present invention is to provide a probe capable of easily performing zero point correction, an optical coherence tomography device, and a zero point correction method.

Solution to Problem

In order to solve the above problems, a probe according to the present invention is a probe used in an optical coherence tomography device which irradiates measurement light to a subject and collects scattered light returning after reflection from the subject, including a scanning means composed of galvanometer mirrors for changing an irradiation direction of the measurement light, wherein the scanning means includes actuators for switching reflecting mirrors, which reflect the measurement light, between a state in which the measurement light is reflected by the subject and returns as the scattered light, and a state in which the measurement light is diffusely reflected within the probe.

With this configuration, the probe includes the actuators capable of switching the reflecting mirrors to the state in which the measurement light is diffusely reflected within the probe, for example, during a non-imaging period, that is, when the subject is not shot. Thus, the measurement light irradiated from the probe can be prevented from returning to the reflecting mirror after reflection from the subject. Therefore, even when the measurement light (laser beam) is irradiated from a collimator during the non-imaging period, the probe can be in a state in which the laser beam does not leak to the outside from the probe, and thus it is safe and can be in a state capable of easily performing zero point correction for removing by software noise (image) of image data displayed on the display screen. Further, for example during an imaging period, since the actuators switch the reflecting mirrors reflecting the measurement light to a state in which the measurement light is reflected by the subject and returns as the scattered light, the probe can be in a state capable of imaging the subject. In this way, since the probe can switch the reflecting mirrors between a state in which the measurement light returns to the reflecting mirrors and a state in which the measurement light does not return to the reflecting mirrors by rotating the reflecting mirrors by the actuators, the shutter for blocking the measurement light is not required, and thus it is possible to reduce the number of components and the cost, and to simplify the structure in the probe.

Further, the actuators preferably rotate at least one of the reflecting mirrors to an angle where the measurement light reflected by the reflecting mirror does not return to the reflecting mirror during a non-imaging period.

With this configuration, since the actuators rotate at least one of the reflecting mirrors to the angle where the measurement light reflected by the reflecting mirror does not return to the reflecting mirror during the non-imaging period, the probe can be in a state in which the measurement light irradiated from the probe does not return to the reflecting mirror after reflection from the subject. Therefore, the probe can be in a state capable of easily performing zero point correction.

Further, the scanning means includes a first galvanometer mirror for reflecting the measurement light introduced into a housing of the probe, and a second galvanometer mirror for reflecting the measurement light reflected by the first galvanometer mirror to a nozzle, and wherein the actuators rotate at least one of the first galvanometer mirror and the second galvanometer mirror to an angle where the measurement light does not return to the first galvanometer mirror or the second galvanometer mirror during a non-imaging period.

With this configuration, since the actuators in the probe tilt at least one of reflecting mirrors of the first galvanometer mirror and the second galvanometer mirror to an angle where the measurement light does not return to the reflecting mirror during the non-imaging period, the irradiated measurement light is prevented from returning to the reflecting mirror. Therefore, it is possible to easily perform zero point correction during the non-imaging period.

Further, the probe is preferably provided with a switch for correcting zero point of image data of the optical coherence tomography device in a state in which at least one of the reflecting mirrors is inclined at an angle where the measurement light reflected by the reflecting mirror does not return to the reflecting mirror.

With this configuration, it is possible to correct zero point of the image data of the optical coherence tomography device by operating the switch provided on the probe, thereby easily correcting zero point.

An optical coherence tomography device according to the present invention corrects zero point, by obtaining background data in the state in which the measurement light is diffusely reflected within the probe, and by subtracting the background data from measurement data obtained in a state in which the reflecting mirrors reflecting the measurement light are inclined so that the measurement light is reflected by the subject and returns as the scattered light.

With this configuration, the optical coherence tomography device performs zero point correction by subtracting the background data, which is obtained in a state in which the measurement light is diffusely reflected within the probe, from the measurement data which is obtained in a state in which the irradiated measurement light is reflected by the subject and returns as the scattered light, and thus it is possible to adjust the image to appear more clearly.

Further, the optical coherence tomography device is preferably provided with a foot controller for obtaining background data in a state in which at least one of the reflecting mirrors is inclined at an angle where the measurement light reflected by the reflecting mirror does not return to the reflecting mirror.

With this configuration, since an operator can obtain the background data by operating the foot controller without using hands, the optical coherence tomography device can easily perform zero point correction.

Further, a zero point correction method according to the present invention corrects zero point, by obtaining background data in the state in which the measurement light is diffusely reflected within the probe, and by subtracting the background data from measurement data which is obtained in a state in which the reflecting mirrors reflecting the measurement light are inclined so that the measurement light is reflected by the subject and returns as the scattered light.

With this configuration, since the zero point correction method can perform zero point correction without adding a special component by subtracting the background data, which is obtained in a state in which the measurement light is diffusely reflected within the probe, from the measurement data which is obtained in a state in which the irradiated measurement light is reflected by the subject and returns as the scattered light, the structure in the probe is not complicated.

Advantageous Effects of Invention

According to the present invention, it is possible to provide a probe capable of easily performing zero point correction, an optical coherence tomography device, and a zero point correction method.

DESCRIPTION OF EMBODIMENTS

Hereinafter, embodiments of the present invention will be described with reference to FIGS. 1 to 6. Before describing a probe according to the embodiment of the present invention, an OCT device 100 (optical coherence tomography device), in which a probe 1 (diagnostic probe unit) is used, will be described with reference to FIG. 6. For convenience, in a state of the probe 1 (diagnostic probe unit) shown in FIG. 1, it is assumed that a direction in which a nozzle 40 is disposed is "front", a direction in which a tubular body 20 is disposed is "rear", a vertically upper side is "upper", a vertically lower side is "lower", and width directions are "left" and "right".

<<OCT Device>>

Figure 6:
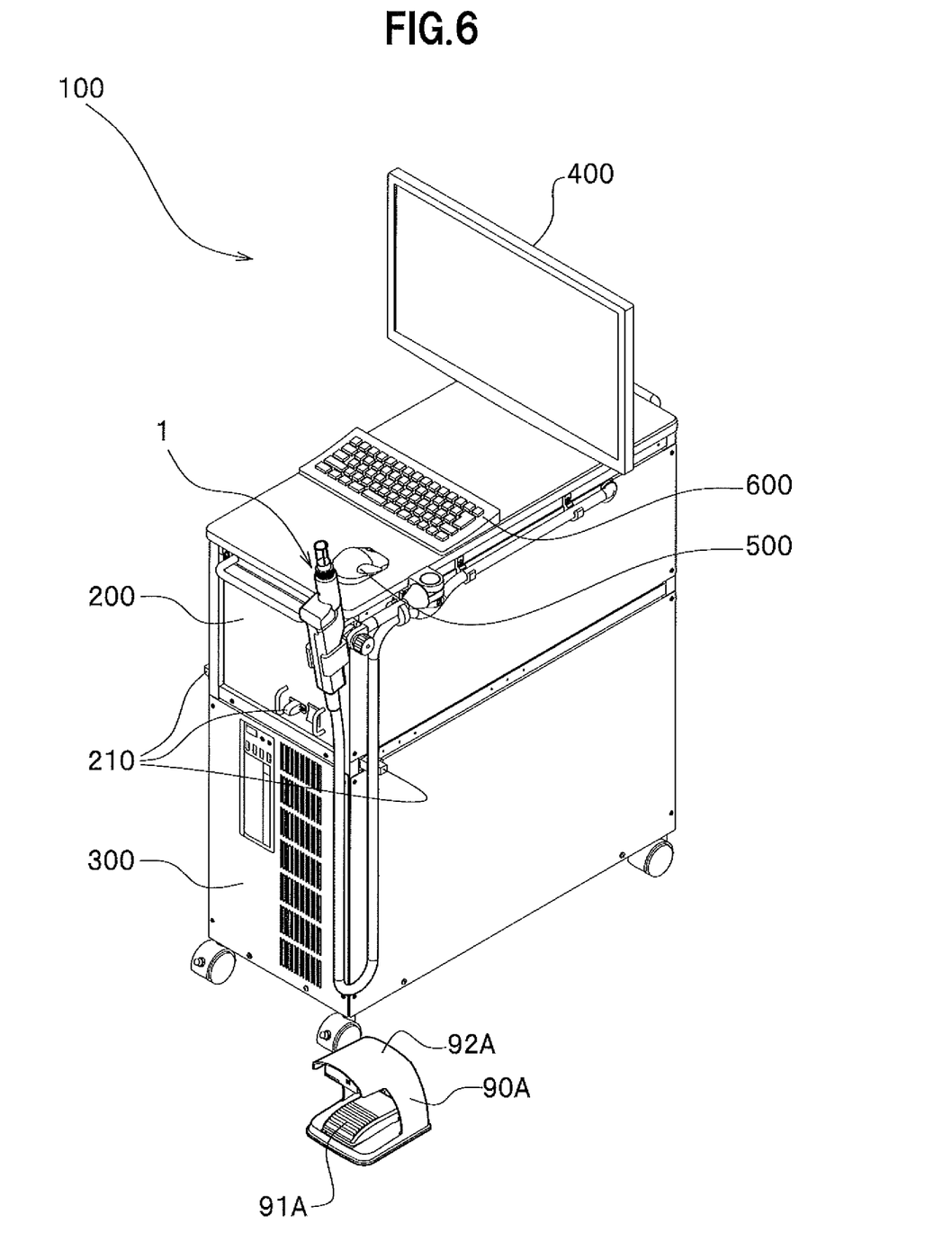
FIG. 6 is an external view showing a first modification of an optical coherence tomography device according to the embodiment of the present invention.

The OCT device 100 shown in FIG. 6 is used as an imaging device for capturing a tomographic image of a subject (sample) such as a tooth (front tooth), a molar tooth and oral tissue of a dental patient. The OCT device 100 is a device for capturing the tomographic image of the subject using coherent light. The OCT device 100 mainly includes the probe 1, an optical unit 200, a control unit 300, and a display unit 400 for displaying a captured tomographic image. The OCT device 100 distributes a laser beam irradiated from a light source into measurement light and reference light in the optical unit 200. The measurement light is irradiated to the subject from the probe 1, and returns as scattered light after reflection from the subject, and is then collected by the probe 1. Further, the reference light is irradiated to a reference mirror in the optical unit 200. Then, the optical unit 200 combines the scattered light and a reflected light from the reference mirror into interference light by an optical multiplexer, and the control unit 300 analyzes the interference light, to generate the tomographic image. Note that, the OCT device 100 has a function capable of performing zero point correction for removing by software noise (image) of image data displayed on a display screen of the display unit 400.

Further, a control unit (not shown) of the OCT device 100 includes a galvanometer mirror control circuit for switching the probe 1 between a non-imaging mode in a state in which the laser beam does not leak to the outside of the probe 1 so that the zero point correction can be performed, and an imaging mode in a state in which the measurement light is irradiated to the subject from the probe 1 and returns as the scattered light after reflection from the subject. The galvanometer mirror control circuit is a control circuit for changing angles of a first galvanometer mirror 72 and a second galvanometer mirror 73 to predetermined angles by driving actuators 72b, 73b of a scanning means 70 shown in FIGS. 2 and 3.

<<Probe>>

Figure 1:
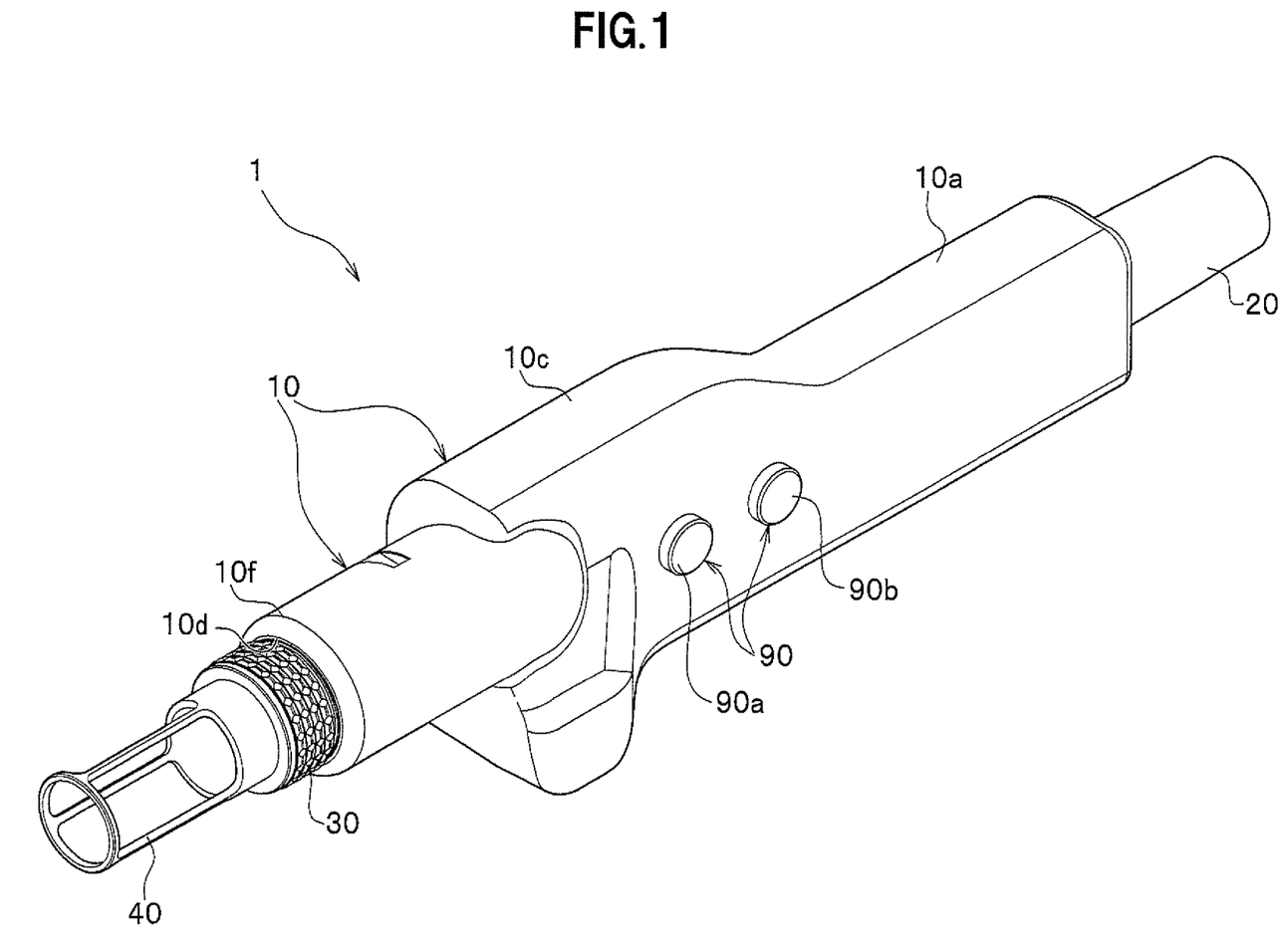
FIG. 1 is an external view of a probe according to an embodiment of the present invention.
Figure 2:
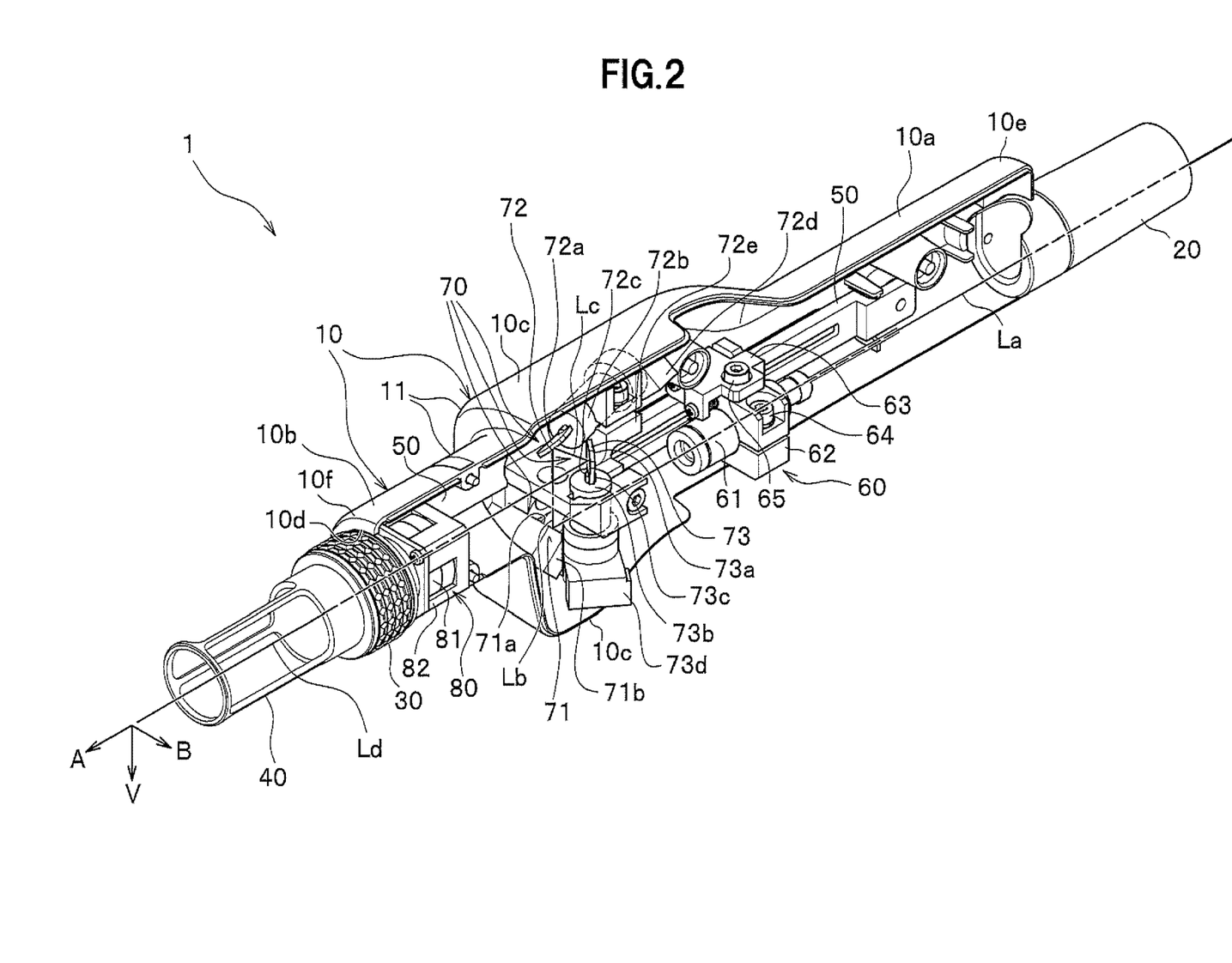
FIG. 2 is a perspective view showing a state after removing a housing half of the probe according to the embodiment of the present invention.
Figure 3:
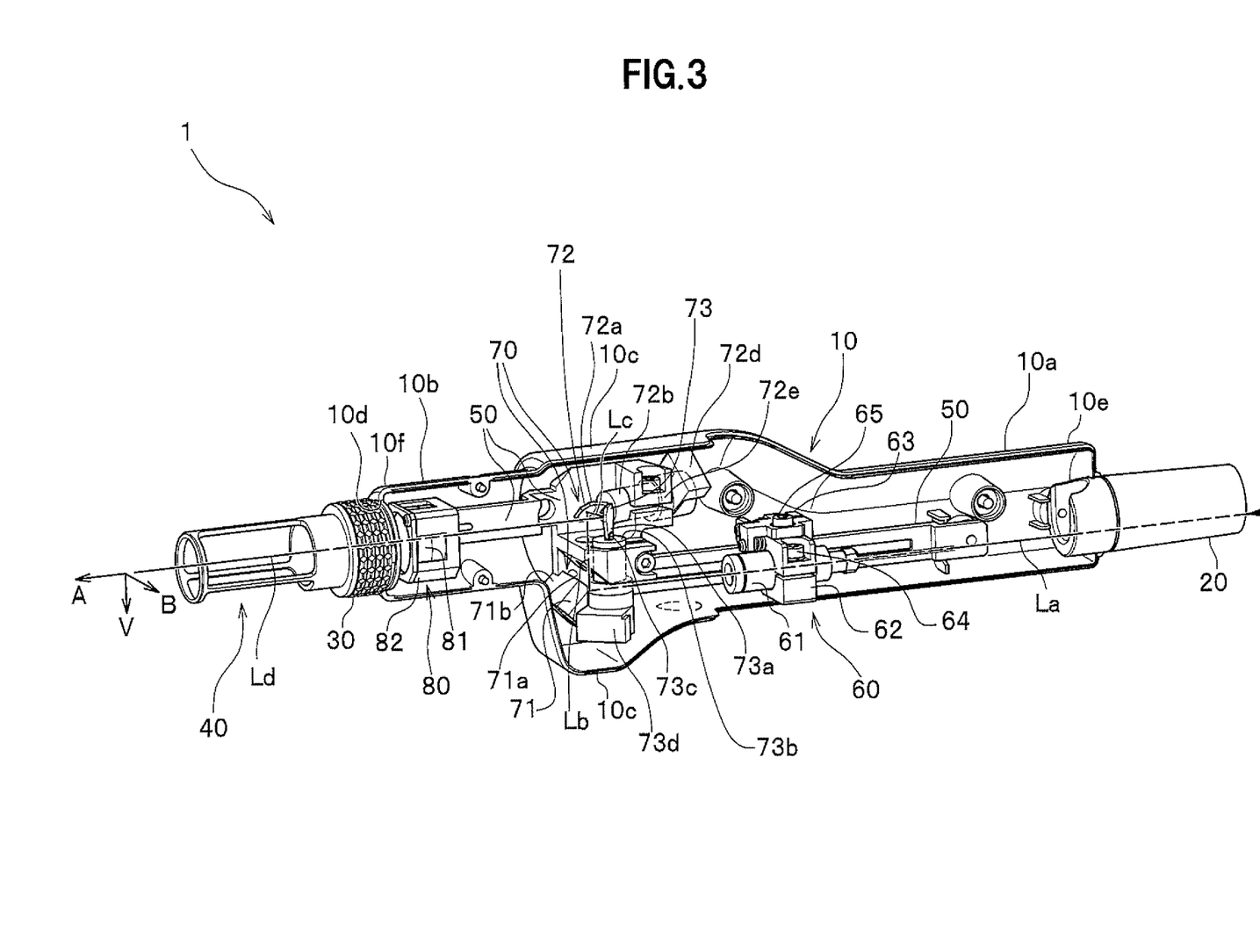
FIG. 3 is a perspective view showing the state after removing the housing half of the probe according to the embodiment of the present invention.

As shown in FIGS. 2 and 3, the probe 1 is a diagnostic probe unit, which has the scanning means 70 (galvanometer mirror) for scanning the laser beam two-dimensionally, irradiates the laser beam (measurement light) from the optical unit 200 (see FIG. 6) to the subject, and receives the scattered light returning after reflection from the subject, to introduce it to the optical unit 200. The probe 1 mainly includes a housing 10 in which an optical path of the measurement light and the scattered light is provided, a cylindrical body 20 provided at a proximal end portion 10e of the housing 10, a nozzle support body 30 connected to a distal end portion 10f of the housing 10, a shooting nozzle 40 fitted onto the nozzle support body 30, a frame body 50 provided in the housing 10, a collimator lens 60 disposed close to the proximal end portion 10e side at a substantially middle portion in the housing 10, the scanning means 70 disposed at a substantially middle portion in the housing 10, a condenser lens 80 disposed on the distal end portion 10f side in the housing 10, and a switch 90 (see FIG. 1) for selecting whether or not to perform zero point correction.

The probe 1 is configured such that an operator holds the housing 10 in one's hand (not shown) during an imaging period, so that a distal end portion of the nozzle 40 is brought into contact with a surface of the oral tissue, the measurement light introduced into the housing 10 from the optical unit 200 (see FIG. 6) is irradiated to the oral tissue from the distal end portion of the nozzle 40, and the scattered light returning after reflection from the oral tissue is collected by the nozzle 40, so as to be transmitted to the optical unit 200. Hereinafter, in the present embodiment, a probe including the nozzle 40 (front tooth nozzle) for direct view imaging will be described as an example of the probe 1.

<<Housing>>

As shown in FIGS. 2 and 3, the housing 10 is composed of a hollow case body for covering components such as the frame body 50, the collimator lens 60, the scanning means 70 and the condenser lens 80, and for supporting the nozzle support body 30 and the switch 90 (see FIG. 1). The housing body 10 has a measurement light introducing portion 10a formed on a side of the proximal end portion 10e into which the measurement light is introduced, a condenser lens housing portion 10b formed on a side of the distal end portion 10f in which the nozzle 40 and the like are arranged, a scanning means housing portion 10c in which the scanning means 70 is housed, and an opening portion 10d into which the nozzle support body 30 is inserted. The housing 10 is formed by fitting two case halves 11, 12 (see FIG. 1) to each other, the case halves having a shape obtained by longitudinally dividing a central portion of the housing 10 into left and right. For example, the housing 10 is formed in a straight shape so that an optical axis La of the measurement light introduced into the measurement light introducing portion 10a to the scanning means 70, and an optical axis Ld of the measurement light from the scanning means 70 to the opening portion 10d formed at a distal end of the condenser lens housing portion 10b, are aligned in a longitudinal direction.

The measurement light introducing portion 10a is a portion in which an optical fiber, a cable and the like (not shown) are provided, and is formed in a rectangular tube shape. The condenser lens housing portion 10b is a portion for housing the condenser lens 80, which collects the measurement light being reflected in the scanning means 70 and irradiates the light to the subject, and is formed in a substantially cylindrical shape.

The scanning means housing portion 10c is a portion for housing the scanning means 70 disposed at the substantially middle portion of the housing 10, and is formed between the measurement light introducing portion 10a and the condenser lens housing portion 10b. On a side surface of the scanning means housing portion 10c of the housing 10, switch knobs 90a, 90b of the switch 90 (see FIG. 1) are provided for selecting whether or not to perform zero point correction when reflecting mirrors 72a, 73a are inclined at an angle where the measurement light does not return.

<<Cylindrical Body>>

As shown in FIGS. 2 and 3, the cylindrical body 20 is a substantially cylindrical member which is fitted into the proximal end portion 10e of the measurement light introducing portion 10a at a distal end side thereof. Into the cylindrical body 20, the cable for electrically connecting the probe 1, the optical unit 200 (see FIG. 6) and the control unit (not shown), and the optical fiber which is optically connected to the optical unit 200, are inserted.

<<Nozzle Support Body>>

The nozzle support body 30 is a member for allowing the housing 10 to support the nozzle 40, and is formed in a substantially cylindrical shape. Note that, the nozzle support body 30 only has to be one capable of detachably attaching the nozzle 40 to the distal end portion 10f of the housing 10 by a connecting member, and a structure thereof is not particularly limited.

<<Nozzle>>

The nozzle 40 is a substantially cylindrical member for irradiating the measurement light from the scanning means 70 to the subject and collecting the scattered light, and is inserted into the nozzle support body 30 at a proximal end thereof. The nozzle 40 is, for example, composed of a direct view imaging nozzle used for imaging the front tooth. Note that, the nozzle 40 may be the direct view imaging nozzle or a side view imaging nozzle used for imaging the molar tooth, and is replaceable with the side view imaging nozzle by attaching and detaching.

<<Frame Body>>

The frame body 50 is a thick plate member for holding the collimator lens 60, the scanning means 70 and the condenser lens 80, and is screwed to an inner wall of the housing 10. The frame body 50 is formed in a substantially straight shape in side view in accordance with the shape of the housing 10.

<<Collimator Lens>>

As shown in FIGS. 2 and 3, the collimator lens 60 is a lens for receiving the measurement light introduced into the measurement light introducing portion 10*a* from the optical fiber (not shown), and for converging the measurement light into a parallel light. The collimator lens 60 includes a collimator 61, a collimator holder 62, a collimator bracket 63, a holder fastener 64 for fastening the collimator 61, a bracket fastener 65 for fastening the collimator holder 62, and a frame fastener (not shown) for fastening the collimator bracket 63. Note that, the collimator lens 60 can adjust its position in an optical axis direction and its inclination with respect to the optical axis La, and can adjust an inclination of the optical axis La and an optical path length of the measurement light.

<<Scanning Means>>

As shown in FIGS. 2 and 3, the scanning means 70 is a device for changing an irradiation direction of the measurement light introduced into the housing 10, and is configured to include two galvanometer mirrors (first galvanometer mirror 72 and second galvanometer mirror 73) arranged at the substantially middle portion in the optical axis direction in the housing 10. The scanning means 70 is mainly composed of a mirror 71 for reflecting the measurement light introduced into the housing 10, the first galvanometer mirror 72 for reflecting the measurement light reflected by the mirror 71, and the second galvanometer mirror 73 for reflecting the measurement light reflected by the first galvanometer mirror 72 to the nozzle 40.

<Mirror>

The mirror 71 is fixed to a lower portion in the scanning means housing portion 10*c* of the housing 10 in a state of tilting a mirror surface thereof at 45 degrees with respect to the optical path of the measurement light. The mirror 71 includes a mirror body 71*a* having a mirror surface, and a mirror case 71*b* for holding the mirror body 71*a*. The mirror body 71*a* is disposed such that the mirror surface is upwardly inclined at 45 degrees with respect to the optical axis La so as to convert the optical axis La of the measurement light, which is introduced into the housing 10 and transmitted through the collimator lens 60, into an optical axis Lb by 90 degrees.

<First Galvanometer Mirror and Second Galvanometer Mirror>

As shown in FIGS. 2 and 3, the first galvanometer mirror 72 is composed of a galvanometer mirror (also referred to as a "galvanometer scanner") having the reflecting mirror 72*a* for converting the optical axis Lb of upward measurement light reflected by the mirror 71 to a lateral direction by 90 degrees. The second galvanometer mirror 73 is composed of a galvanometer mirror for converting an optical axis Lc converted by the first galvanometer mirror 72 to a front direction of the optical axis Ld by 90 degree. The first galvanometer mirror 72 and the second galvanometer mirror 73 (scanning means 70) include the reflecting mirrors 72*a*, 73*a*, the actuators 72*b*, 73*b* for rotating the reflecting mirrors 72*a*, 73*a*, encoders (not shown) provided in rotating shafts 72*c*, 73*c* of the actuators 72*b*, 73*b* having the reflecting mirrors 72*a*, 73*a* on distal ends thereof, connectors 72*d*, 73*d* for connecting the actuators 72*b*, 73*b*, the encoders (not shown) and the control unit (not shown), and a galvanometer mirror holder 72*e* for holding the actuator 72*b*.

The reflecting mirrors 72*a*, 73*a* are galvanometer mirror bodies for reflecting the measurement light. The reflecting mirror 72*a* of the first galvanometer mirror 72 reflects the measurement light from the mirror 71 to the second galvanometer mirror 73 during an imaging period. The reflecting mirror 73*a* of the second galvanometer mirror 73 reflects the measurement light from the first galvanometer mirror 72 to the condenser lens 80 during the imaging period.

Figure 4A:
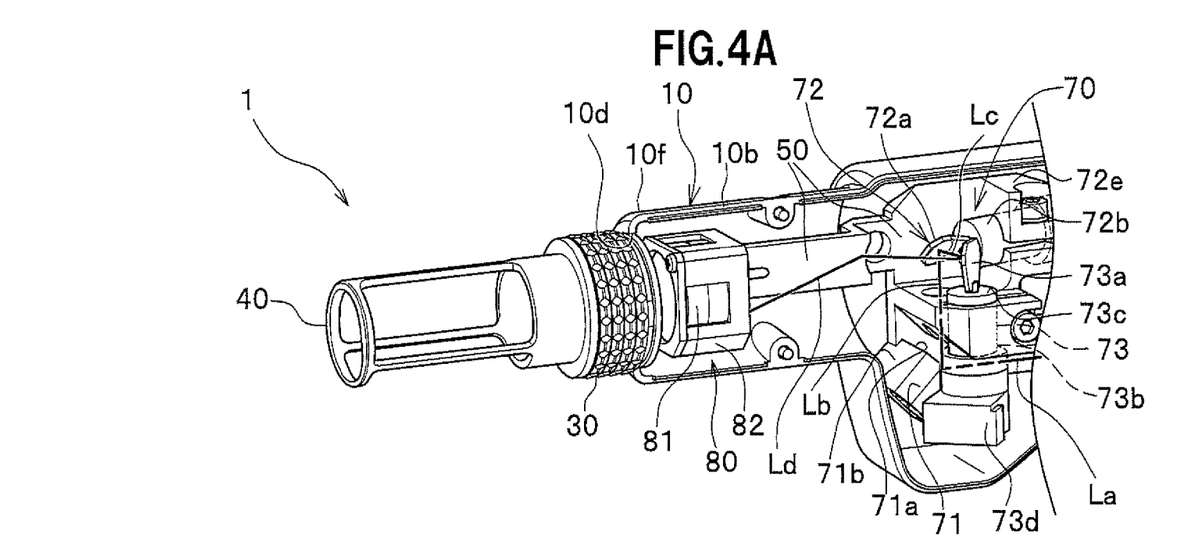
FIG. 4A is a view showing a part of the probe during a non-imaging period and is a perspective view of a main part showing the state after removing the housing half.
Figure 4B:
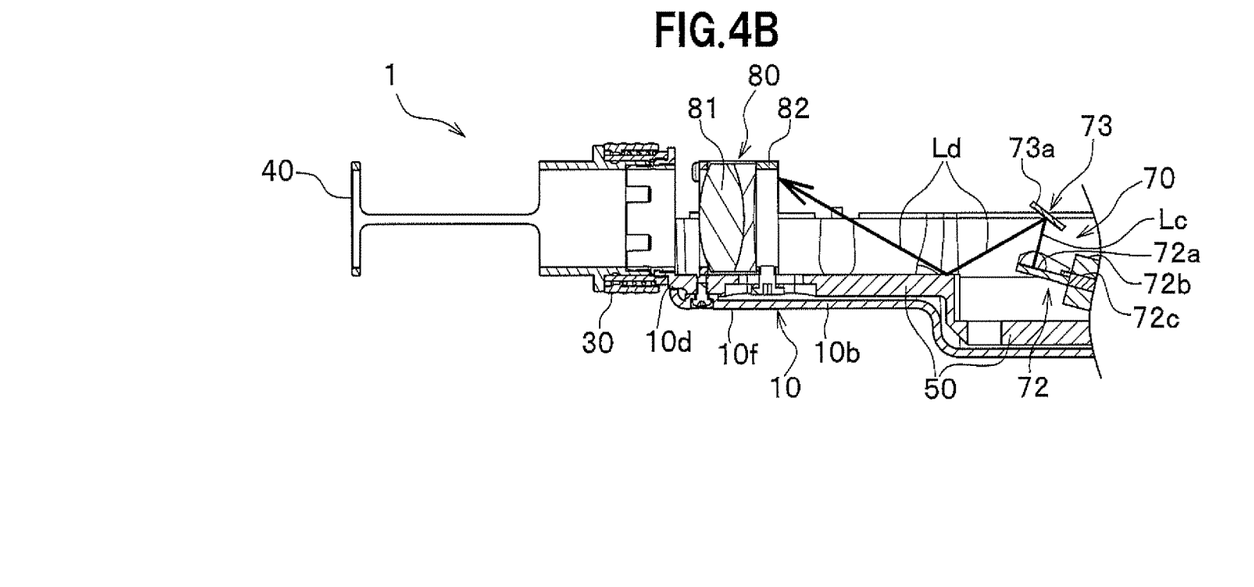
FIG. 4B is a view showing the part of the probe during the non-imaging period and is a cross-sectional view of a main part showing an optical axis of measurement light.
Figure 5A:
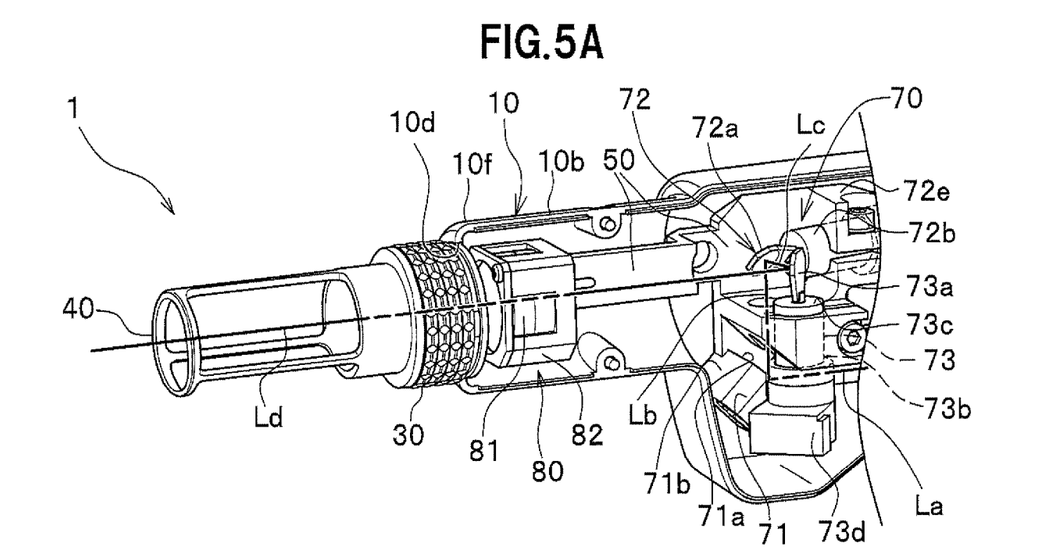
FIG. 5A is a view showing the part of the probe during an imaging period and is a perspective view of the main part showing the state after removing the housing half.
Figure 5B:
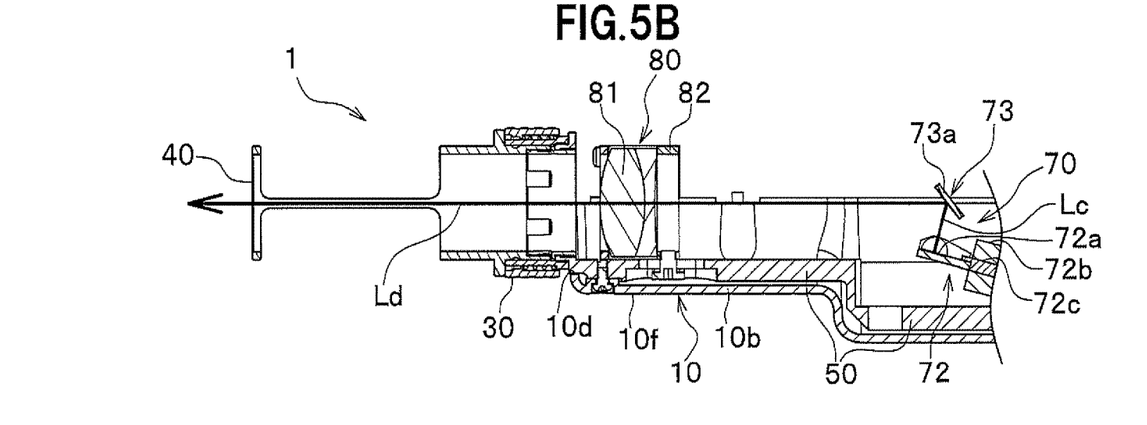
FIG. 5B is a view showing the part of the probe during the imaging period and is a cross-sectional view of the main part showing the optical axis of the measurement light.

The actuators 72*b*, 73*b* are power sources for rotating the reflecting mirrors 72*a*, 73*a*, and are composed of, for example, small electric motors. The actuators 72*b*, 73*b* are connected to the control unit (not shown) including a driver and control function. As shown in FIGS. 4A, 4B, during a non-imaging period, the actuators 72*b*, 73*b* are driven by a drive signal from the control unit (not shown) to rotate the reflecting mirrors 72*a*, 73*a*, so that the reflecting mirrors 72*a*, 73*a* are switched to an inclined state in which the measurement light does not return to the reflecting mirrors 72*a*, 73*a*. Further, as shown in FIGS. 5A, 5B, during the imaging period, the actuators 72*b*, 73*b* are driven by a drive signal from the control unit (not shown) to rotate the reflecting mirrors 72*a*, 73*a*, so that the reflecting mirrors 72*a*, 73*a* are switched to an inclined state in which the measurement light is irradiated to the subject and the scattered light reflected from the subject returns to the probe 1.

Further, the actuator 72*b* of the first galvanometer mirror 72 shown in FIGS. 2 and 3 has an angle adjustment function of adjusting an angle with respect to the optical axis Lb by rotating a mirror surface of the reflecting mirror 72*a* around an axis in an A direction. The actuator 73*b* of the second galvanometer mirror 73 has an angle adjustment function of adjusting an angle with respect to the optical axis Lc by rotating a mirror surface of the reflecting mirror 73*a* around an axis in a V direction.

Note that, during the non-imaging period, the actuators 72*b*, 73*b* only have to switch at least one of the reflecting mirror 72*a* of the first galvanometer mirror 72 and the reflecting mirror 73*a* of the second galvanometer mirror 73 to the inclined state in which the measurement light does not return to the reflecting mirrors 72*a*, 73*a* by rotating the reflecting mirrors 72*a*, 73*a*. Hereinafter, during the non-imaging period, a case will be described as an example, in which the actuator 73*b* of the second galvanometer mirror 73 switches the reflecting mirror 73*a* to the state in which the measurement light does not return by rotating the reflecting mirror 73*a*.

The rotating shafts 72*c*, 73*c* are shafts rotated by the actuators 72*b*, 73*b*, and are provided with digital encoders (not shown) for detecting inclined positions of the reflecting mirrors 72*a*, 73*a* at proximal ends thereof. On the rotating shafts 72*c*, 73*c*, the galvanometer mirrors are fixed to distal end sides thereof, and the actuators 72*b*, 73*b* are disposed on proximal end sides thereof. Note that, the encoders (not shown) are devices for detecting rotation angles of the rotating shafts 72*c*, 73*c*, and may be position sensors for detecting the rotation angles of the rotating shafts 72c, 73c other than the digital encoders.

The connectors 72d, 73d are portions to which mating connectors are attached, each of the mating connectors being attached to one end of a cable which is electrically connected to the control unit (not shown) at the other end of the cable. The galvanometer mirror holder 72e of the first galvanometer mirror 72 is a member for holding a proximal end of the actuator 72b, and is screwed to the frame body 50.

<<Condenser Lens>>

As shown in FIGS. 2 and 3, the condenser lens 80 is composed of a lens body 81 and a lens housing body 82, and is housed in a position close to the distal end of the condenser lens housing portion 10b of the housing 10. Further, the condenser lens 80 has a function of a condensing point adjustment mechanism capable of adjusting a position (distance) of a condensing point of the condenser lens 80 in the optical axis direction. Therefore, by adjusting a distance between the condenser lens 80 and the subject (front tooth portion) by moving the condenser lens 80 in the optical axis direction, it is possible to adjust the condensing point of the measurement light with respect to the subject. The condenser lens 80 is a lens for collecting scanning light from the scanning means 70 and for irradiating the collected measurement light to the subject.

<<Switch>>

The switch 90 (see FIG. 1) is a switch for outputting a command signal to correct zero point of the image data of the OCT device 100 (see FIG. 6) in a state in which the reflecting mirror 73a is inclined at an angle where the measurement light reflected by the reflecting mirror 73a does not return to the reflecting mirror 73a. As shown in FIG. 1, the switch 90 is, for example, configured to include two switch knobs 90a, 90b arranged in parallel in the housing 10. The switch knobs 90a, 90b are knobs for performing an operation to select "YES/NO" of whether or not to perform zero point correction, and the switch knob 90a is for "YES" and the switch knob 90b is for "NO".

[Operation]

Next, operation of the probe 1 will be described with an example of imaging the subject which is the oral tissue such as tooth portion and gingiva.

First, before imaging the subject such as a front tooth of a patient by the probe 1, the operator performs zero point correction, which is calibration of the image data displayed on the display screen before recording the data. When optical noise or the like as background data is measured and zero point correction for removing the noise (image) of the image data is performed, a measurement switch (not shown) displayed on the screen of the display unit 400 of the OCT device 100 shown in FIG. 6 is operated by a mouse 500 or a keyboard switch 600. Then, a switch signal is sent from the measurement switch to the control unit 300, and the control unit 300 sends the drive signal to the actuator 73b of the second galvanometer mirror 73, and rotates the actuator 73b, so that the reflecting mirror 73a is in the non-imaging mode in which the reflecting mirror 73a is inclined at the angle where the measurement light reflected by the reflecting mirror 73a does not return to the reflecting mirror 73a.

When the reflecting mirror 73a of the second galvanometer mirror 73 is switched to the non-imaging mode in which the reflecting mirror 73a is inclined at an angle where the measurement light does not return, even when the measurement light is irradiated in this state, as shown in FIGS. 4A, 4B, the measurement light reflected by the reflecting mirror 73a is reflected toward an inner wall surface of the housing 10 and then is diffusedly reflected by the inner wall surface.

The measurement light diffusedly reflected in the probe 1 instantaneously becomes weak light. Therefore, the measurement light reflected by the reflecting mirror 73a is only slightly reflected toward the nozzle 40 and the condenser lens 80, and even when the measurement light hits the subject such as the front tooth, it does not return to the reflecting mirror 73a of the second galvanometer mirror 73 through the nozzle 40 and the condenser lens 80.

Note that, zero point correction described below is affected by the scattered light, which is the measurement light reflected by the subject, when the scattered light returns to an exit port. However, a size of the exit port through which the measurement light passes is small, that is, equal to or smaller than 100 μm core diameter of the optical fiber, and thus the measurement light never return to the exit port.

Therefore, when the probe 1 is in the non-imaging mode, the measurement light which is diffusedly reflected in the probe 1 does not affect zero point correction. Further, when the probe 1 is in the non-imaging mode, even when the measurement light (laser beam) is accidentally irradiated, the measurement light sent in the probe 1 is not irradiated outwardly from the probe 1.

When the operator switches the OCT device 100 (see FIG. 6) to this non-imaging mode and presses the switch knob 90a shown in FIG. 1, the command signal for correcting zero point of the image data is sent from the switch 90 to the control unit 300 of the OCT device 100, so that the zero point correction is performed. In the zero point correction, in a state in which the reflecting mirror 73a (see FIGS. 2 and 3) of the probe 1 is inclined at the angle where the measurement light does not return to the reflecting mirror 73a, the background data in the state in which the measurement light is diffusely reflected in the probe 1 is obtained, and the background data is subtracted from measurement data, that is, the data which is obtained in a state in which the measurement light is reflected by the subject and returns as the scattered light, so that the zero point correction is performed. In this way, by subtracting the background data from the data recorded, it is possible to perform the calibration for reducing influence of the noise generated in the background.

Further, when imaging the subject, the operator drives the OCT device 100 (see FIG. 6), and then holds the measurement light introducing portion 10a or the scanning means housing portion 10c of the probe 1 shown in FIG. 1, to bring the distal end portion of the nozzle 40 into contact with the front tooth. When the operator turns on a drive switch (not shown) to drive the OCT device 100 (see FIG. 6), the OCT device 100 sends a drive signal to the control unit (not shown), and the control unit drives the actuator 73b of the second galvanometer mirror 73 to rotate the rotating shaft 73c of the reflecting mirror 73a to a normal state position during the imaging period, so that the probe 1 is switched to the imaging mode.

When the measurement light is irradiated in this imaging mode, as shown in FIGS. 5A, 5B, the measurement light introduced into the probe 1 is reflected to an angular direction of a center of the condenser lens 80 by the mirror body 71a (see FIGS. 2 and 3) of the mirror 71, the reflecting mirror 72a of the first galvanometer mirror 72, and the reflecting mirror 73a of the second galvanometer mirror 73, so as to be irradiated to the subject from the nozzle 40.

The OCT device 100 (see FIG. 6) collects the scattered light returning after reflection from the subject by the distal end portion of the nozzle 40, transmits the scattered light to the optical unit 200 (see FIG. 6), combines the scattered light and the reflected light from the reference mirror by the optical multiplexer, and analyzes interference light thereof, to generate the tomographic image.

Thus, the probe 1 is forcedly switched to the non-imaging mode by operating the measurement switch (not shown) of the display unit 400, by driving the actuator 73b of the second galvanometer mirror 73 of the scanning means 70, and by rotating the reflecting mirror 73a to the angle where the measurement light reflected by the reflecting mirror 73a does not return to the reflecting mirror 73a. Then, it is possible to easily perform zero point correction by operating the switch knob 90a of the switch 90.

The probe 1 configured as described above is not required to be provided with a device such as a shutter mechanism for blocking the measurement light, and thus it is possible to simplify a structure inside the housing 10, thereby reducing a size of an entire device.

[First Modification]

Figure 7A:
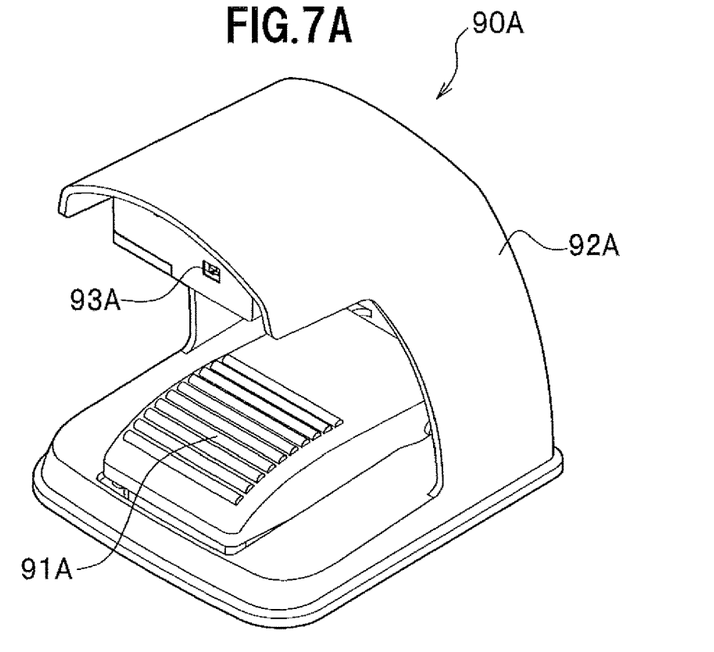
FIG. 7A is an enlarged perspective view of a foot switch shown in FIG. 6.
Figure 7B:
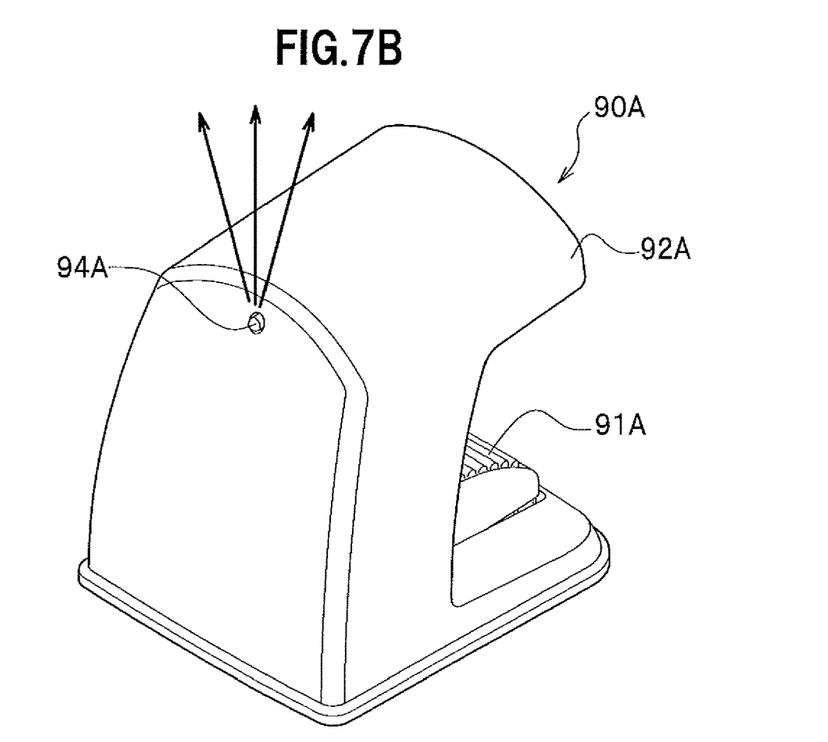
FIG. 7B is an enlarged perspective view of the foot switch as viewed from a rear.
Figure 8:
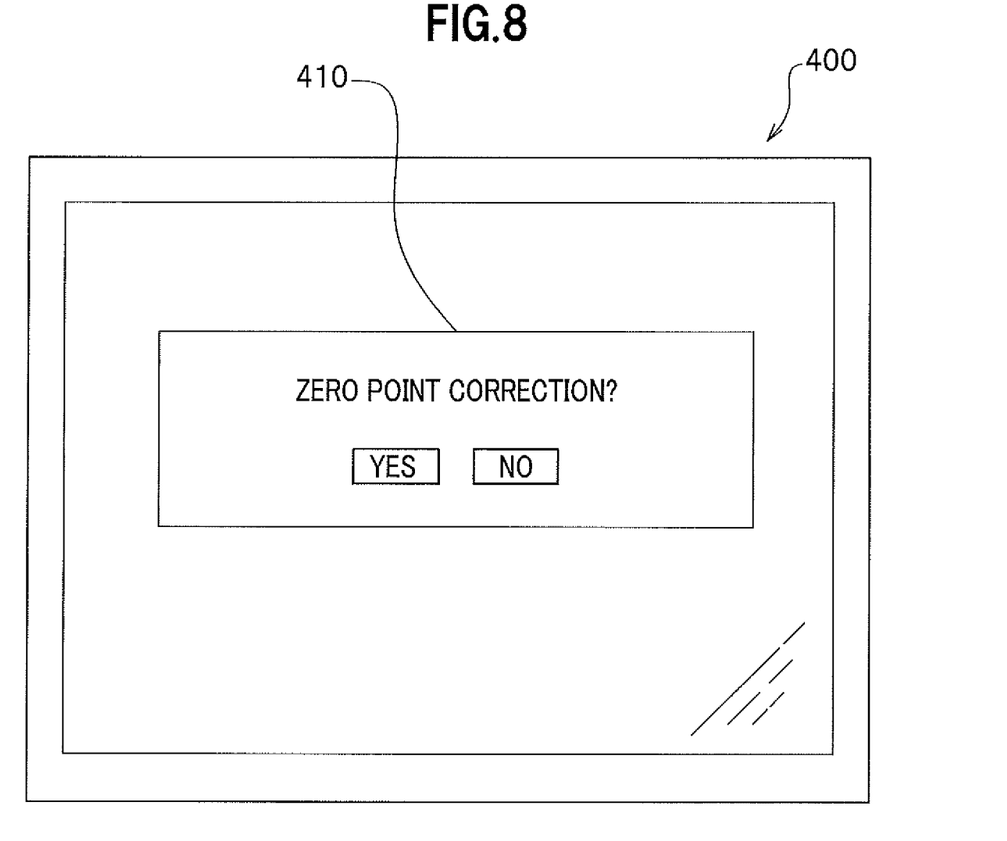
FIG. 8 is an explanatory view showing an example of a screen of a display unit of the optical coherence tomography device.

Note that, the present invention is not limited to the above-described embodiment, but can be variously modified or changed within the scope of the technical concept, and is extended to these modified or changed inventions. FIG. 6 is a view showing a first modification of the probe according to the embodiment of the present invention, and is an external view of the optical coherence tomography device. FIG. 7A is an enlarged perspective view of a foot switch shown in FIG. 6, and FIG. 7B is an enlarged perspective view of the foot switch as viewed from a rear. FIG. 8 is an explanatory view showing an example of the screen of the display unit of the optical coherence tomography device.

Further, as an example of the switch 90 (see FIG. 1), a case where the switch 90 is provided at the housing 10 has been described, however, it may be a foot controller (switch 90A) shown in FIGS. 6, 7A and 7B.

As shown in FIG. 6, the switch 90A is the foot controller having a foot-operated switch knob 91A capable of operating the switch even if the operator cannot use both hands, and has a function of an infrared sensor switch composed of an infrared transmitter 94A and an infrared receiver 210. The switch 90A is a switch for correcting zero point of the image data of the display unit 400 of the OCT device 100 in a state in which the reflecting mirror 73a is inclined at the angle where the measurement light reflected by the reflecting mirror 73a does not return to the reflecting mirror 73a. For example, the switch 90A is communicatively connected to the infrared receiver 210 of the control unit 300 or the optical unit 200 of the OCT device 100 by wire or wirelessly. The infrared receiver 210 is a unit for performing a switching function the same as the switch 90 of the embodiment, and is configured to include a light receiving IC or the like for receiving an infrared switch signal from the infrared transmitter 94A.

As shown in FIGS. 7A, 7B, for example, the switch 90A includes the switch knob 91A, a switch case 92A having a portion into which the operator's toe is inserted, a switch power supply 93A having an exposed tip end provided in the switch case 92A, and the infrared transmitter 94A.

The switch knob 91A is the knob of the foot switch of two-step depression type, and selects "YES/NO", that is, whether or not to perform zero point correction by a depression amount of foot depression operation. For example, the switch knob 91A emits a switch signal of "NO" not to perform zero point correction, when the knob is not depressed to a second step position even when the knob is depressed to a first step position. When the knob is depressed to the second step position, the switch knob 91A emits a switch signal of "YES" to perform zero point correction.

The switch case 92A is a case body formed substantially U-shaped in a vertical cross-sectional view, and is placed on a floor. The switch case 92A is provided with the switch knob 91A in a bottom surface portion thereof, the switch power supply 93A on a front side of an upper end portion thereof, and the infrared transmitter 94A on a rear side of the upper end portion thereof. The switch power supply 93A is composed of, for example, a small lithium battery or the like.

The infrared transmitter 94A shown in FIG. 7B is, for example, configured to include an LED. The infrared transmitter 94A is provided in the switch case 92A so that it can transmit information only upwardly, and is adapted to be driven when infrared light emitted only in a vicinity of the switch 90A is received by the infrared receiver 210. The infrared transmitter 94A and the infrared receiver 210 constitute a proximity sensor which is turned ON/OFF when a detection object such as the operator approaches.

As shown in FIG. 8, a selection switch 410 for selecting "YES/NO" (whether or not to perform zero point correction) is displayed on the screen of the display unit 400. When "YES" displayed on the screen of the display unit 400 is selected by the mouse 500 or the keyboard switch 600, the selection switch 410 emits the switch signal of "performing zero point correction" to the control unit 300, so that zero point correction is performed.

In addition, in order to select "YES/NO" (whether or not to perform zero point correction), it is also possible to select "YES" by depressing the switch knob 91A of two-step depression type to the second step position. Note that, the switch knob 91A may be determined not to perform zero point correction, when it is not depressed to the second step position within a predetermined time (for example, 5 seconds) after being depressed to the first step position even when it is depressed to the first step position.

The OCT device 100 configured as described above receives infrared light, which is irradiated from the infrared transmitter 94A and is reflected by the operator's leg, by the infrared receiver 210, when the operator moves one's leg within a sensitive preset distance above the switch 90A even when the operator works while holding the probe 1 in one's hand. When the infrared receiver 210 receives the infrared light, the actuators 72b, 73 are driven to switch the reflecting mirror 73a to the non-imaging mode, so that the zero point correction can be performed. Further, by depressing the switch knob 91A of the switch 90A of the foot controller, it is possible to perform zero point correction by selecting "YES/NO" (whether or not to perform zero point correction).

Further, "YES/NO" (whether or not to perform zero point correction) may also be selected by operating the switch 90 provided in the probe 1 of the embodiment similarly to the switch 90A of the foot controller.

Further, the two-step switch 90A of the foot controller may be a general one-step switch. In this case, the switch 90A is in an "ON" state of performing zero point correction when it is depressed by one step.

[Second Modification]

Further, the switch 90 may be a two-step push button switch having one knob similarly to the switch 90A of the foot controller. In this case, the two-step push button switch determines "YES/NO" of zero point correction by an operation amount of depression. For example, the two-step push button switch emits the switch signal of "NO" not to perform zero point correction, when the knob is not depressed to a second step position even when the knob is depressed to a first step position. Further, the two-step push button switch emits the signal of "YES" to perform zero point correction, when the knob is depressed to the second step position.

Further, the switch 90 may be a seesaw switch, a slide switch or the like other than the push button switch, if it is a switch having a plurality of switch positions even if it has one switch knob. Further, the switch 90 may be a general one-step push button switch. In this case, the switch 90 is in an "ON" state when it is pressed by one step. Furthermore, the switch 90 may be provided in a place other than the scanning means housing portion 10c, if it is in the housing 10.

[Third Modification]

In the embodiment, as shown in FIGS. 2 and 3, as an example of the probe 1, the scanning means 70 including the mirror 71, the first galvanometer mirror 72 and the second galvanometer mirror 73 has been described, however, the probe 1 may be one including the scanning means 70 composed of the first galvanometer mirror 72 for reflecting the measurement light introduced into the housing 10 of the probe 1, and the second galvanometer mirror 73 for reflecting the measurement light reflected by the first galvanometer mirror 72 toward the nozzle 40. That is, the scanning means 70 may be one not including the mirror 71.

Also in this case, as with the embodiment, the probe 1 has the actuators 72b, 73b having the angle adjustment function of adjusting the angles of the mirror surfaces by rotating the rotating shafts 72c, 73c of the reflecting mirrors 72a, 73a respectively in the first galvanometer mirror 72 and the second galvanometer mirror 73.

Further, in the embodiment, a case has been described as an example, in which when the switch 90 (see FIG. 1) is operated, the actuator 73b of the second galvanometer mirror 73 is driven so that the reflecting mirror 73a is inclined at the angle where the measurement light does not return to the reflecting mirror 73a, however, the actuator 72b of the first galvanometer mirror 72 may be driven so that the reflecting mirror 72a is inclined. Further, the actuators 72b, 73b of the first galvanometer mirror 72 and the second galvanometer mirror 73 may be driven so that both of the reflecting mirrors 72a, 73a are inclined.

[Other Modifications]

Further, as an example of the actuators 72b, 73b, the electric motors for rotating the rotating shafts 72c, 73c of the reflecting mirrors 72a, 73a have been described, however, if the actuators are drive mechanisms or drive sources capable of changing directions or angles of the mirror surfaces of the reflecting mirrors 72a, 73a, a driving method thereof is not particularly limited. For example, the actuators 72b, 73b may be a stepping motor, a servo motor, an electric actuator such as a linear motor, a hydraulic actuator such as a hydraulic motor driven by hydraulic control, a pneumatic actuator such as a pneumatic motor driven by pneumatic control, or an ultrasonic actuator such as an ultrasonic motor driven by ultrasonic control.

Furthermore, the actuators 72b, 73b may be a mechanism such as a link mechanism, a slide mechanism, a gear mechanism, a cylinder mechanism, or solenoid, for moving the reflecting mirrors 72a, 73a to a position in which the measurement light reflected by the reflecting mirrors 72a, 73a does not return to the reflecting mirrors 72a, 73a by displacing the reflecting minors 72a, 73a (first galvanometer mirror 72, second galvanometer mirror 73) during the imaging period or during the non-imaging period.

In the embodiment and the modifications, as an example of the probe 1, the probe, which is equipped with the nozzle 40 for direct view imaging of the front tooth (incisor) as the subject at the distal end of the housing 10 of a straight shape, has been described, however, it is not limited thereto. The probe 1 may be used by replacing the direct view imaging nozzle with the side view imaging nozzle (molar tooth nozzle) for side view imaging of the molar tooth as the subject.

REFERENCE SIGNS LIST

1: probe
10: housing
40: nozzle
70: scanning means
72: first galvanometer mirror (galvanometer mirror)
72a, 73a: reflecting mirror
72b, 73b: actuator
73: second galvanometer mirror (galvanometer mirror)
90: switch
90A: switch (foot controller)
100: OCT device (optical coherence tomography device)

The invention claimed is:

1. A probe used in an optical coherence tomography device which irradiates measurement light to a subject and collects scattered light that is reflected by the subject and returns into the probe, comprising:
   a scanning means composed of galvanometer mirrors for changing an irradiation direction of the measurement light, the galvanometer mirrors comprising reflecting mirrors which reflect the measurement light to hit the subject and actuators configured to rotate the reflecting mirrors,
   wherein the actuators are rotating the reflecting mirrors within scanning angle ranges so that the scattered light returns into the probe with the measurement light irradiated on the subject when the probe is in a first state and one of the actuators rotates the reflecting mirror to a predetermined angle out of the scanning angle range at which the measurement light is diffusely reflected within the probe when the probe is in a second state.

2. The probe according to claim 1,
   wherein the one of the actuators rotate at least one of the reflecting mirrors to an angle where the measurement light reflected by the reflecting mirror does not return to the reflecting mirror during a non-imaging period.

3. The probe according to claim 2,
   wherein the scanning means comprises:
      a first galvanometer mirror for reflecting the measurement light to have the scattered light introduced into a housing of the probe, the first galvanometer mirror comprising a first reflecting mirror and a first actuator to rotate the first reflecting mirror; and
      a second galvanometer mirror for reflecting the measurement light reflected by the first galvanometer mirror to a nozzle, the second galvanometer mirror comprising a second reflecting mirror and a second actuator to rotate the second reflecting mirror,
   wherein one of the first actuator and the second actuator rotates the first reflecting mirror or the second reflecting mirror to the predetermined angle where the measurement light does not return to the first reflecting mirror or the second reflecting mirror during a non-imaging period.

4. The probe according to claim 1,
   wherein the scanning means comprises:
      a first galvanometer mirror for reflecting the measurement light to have the scattered light introduced into a housing of the probe, the first galvanometer mirror comprising a first reflecting mirror and a first actuator to rotate the first reflecting mirror; and a second galvanometer mirror for reflecting the measurement light reflected by the first galvanometer mirror to a nozzle, the second galvanometer mirror comprising a second reflecting mirror and a second actuator to rotate the second reflecting mirror, wherein one of the first actuator and the second actuator rotates the first reflecting mirror or the second reflecting mirror to the predetermined angle where the measurement light does not return to the first reflecting mirror or the second reflecting mirror during a non-imaging period.

5. The probe according to claim 1, provided with a switch for correcting zero point of image data of the optical coherence tomography device with the probe in the second state in which at least one of the reflecting mirrors is inclined at the predetermined angle where the measurement light reflected by the reflecting mirror does not return to the reflecting mirror.

6. An optical coherence tomography device comprising the probe according to claim 1, wherein the optical coherence tomography device corrects a zero point, by obtaining background data with the probe in the second state in which the measurement light is diffusely reflected within the probe, and by subtracting the background data from measurement data obtained in the first state in which the reflecting mirrors reflecting the measurement light are inclined so that the measurement light hits by the subject to reflect the scattered light.

7. The optical coherence tomography device according to claim 6, provided with a foot controller for obtaining background data with the probe in the second state in which at least one of the reflecting mirrors is inclined at the predetermined angle where the measurement light reflected by the reflecting mirror does not return to the reflecting mirror.

8. A zero point correction method using the probe according to claim 1, which corrects a zero point, by obtaining background data with the probe in the second state in which the measurement light is diffusely reflected within the probe, and by subtracting the background data from measurement data which is obtained with the probe in the first state in which the reflecting mirrors reflecting the measurement light are inclined so that the measurement light hits the subject to reflect the scattered light.

* * * * *